US008658599B2

(12) United States Patent
Insa Boronat et al.

(10) Patent No.: US 8,658,599 B2
(45) Date of Patent: Feb. 25, 2014

(54) PEPTIDE FOR THE PROPHYLACTIC OR THERAPEUTIC TREATMENT OF SKIN TUMORS IN INITIAL STAGES

(75) Inventors: Raul Insa Boronat, Barcelona (ES); Miguel Quintanilla Avila, Madrid (ES); Javier Dotor De Las Herrerías, Cizur Mayor (ES)

(73) Assignee: Digna Biotech, S.L., Pamplona (ES)

( * ) Notice: Subject to any disclaimer, the term of this patent is extended or adjusted under 35 U.S.C. 154(b) by 144 days.

(21) Appl. No.: 13/255,059

(22) PCT Filed: Mar. 4, 2010

(86) PCT No.: PCT/ES2010/070121
§ 371 (c)(1),
(2), (4) Date: Nov. 17, 2011

(87) PCT Pub. No.: WO2010/100310
PCT Pub. Date: Sep. 10, 2010

(65) Prior Publication Data
US 2012/0065144 A1 Mar. 15, 2012

(30) Foreign Application Priority Data
Mar. 6, 2009 (ES) .................................. 200900694

(51) Int. Cl.
*A61K 38/10* (2006.01)
(52) U.S. Cl.
USPC .......................... 514/19.3; 514/18.6; 514/21.5
(58) Field of Classification Search
None
See application file for complete search history.

(56) References Cited

U.S. PATENT DOCUMENTS

2009/0263410 A1* 10/2009 Borras Cuesta et al. ... 424/185.1
2011/0293557 A1* 12/2011 Prieto Valtuena et al. ... 424/85.2

FOREIGN PATENT DOCUMENTS

| EP | 1974740 A1 | 10/2008 |
|---|---|---|
| WO | 0031135 A1 | 6/2000 |
| WO | WO2005084712 A2 | 9/2005 |
| WO | 2007048857 A1 | 5/2007 |
| WO | WO2009150284 A2 | 12/2009 |

OTHER PUBLICATIONS

Definition of derivative from http://cancerweb.ncl.ac.uk/omd/about.html, pp. 1-5. Accessed Jul. 7, 2005.*
Introduction to Cancer from Merck Manual, p. 1. Accessed Mar. 5, 2008.*
Clinical Aspects of Cancer from Merck manual, pp. 1-4. Accessed Mar. 5, 2008.*
Chronic Effects of Sunlight for Actinic Keratoses from Merck Manual, pp. 1-2. Accessed May 22, 2013.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Druekes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Jain RK, "Barriers to Drug Delivery in Solid Tumors," Scientific American, Jul. 1994, 58-65.*
Auerbach R, Nasim A, Lewis RL, Shinners BL, "Angiogenesis assays: problems and pitfalls," Cancer and Metastasis Reviews, 2000, 19: 167-172.*
Gura T, "Systems for Identifying New Drugs Are Often Faulty," Science, Nov. 7, 1997, 28: 1041-1042.*
R. J. Akhurst, Large and small molecule inhibitors of transforming growth factor-[beta] signaling, Current Opinion in Investigational Drugs, Pharmapress, US, Jan. 1, 2006, pp. 513-521, vol. 7, No. 6, XP008127792, ISSN: 1472-4472.
G. Han, "Distinct mechanisms of TGF-1-mediated epithelial-to-mesenchymal transition and metastasis during skin carcinogenesis", Journal of Clinical Investigation, Jul. 1, 2005, pp. 1714-1723, vol. 115, No. 7, XP55040626, ISSN: 0021-9738, DOI: 10.1172/JCI24399, [http://dx.doi.org/10.1172/JCI24399].
Supplemental Extended European Search Report and Opinion of the European Patent Office Application No. 1074870.3-2107 / 2404611 PCT/ES2010070121 issued by the European Patent Office, Munich, Germany, dated Oct. 18, 2012.
W. Cui et al., "TGFbeta1 inhibits the formation of benign skin tumors, but enhances progression to invasive spindle carcinomas in transgenic mice", Cell Aug. 1996, vol. 86, pp. 531-542, Cell Press.
G. Portella et al., "Transforming growth factor beta is essential for spindle cell conversion of mouse skin carcinoma in vivo: implications for tumor invasion", Cell. Growth. Differ. May 1998, vol. 9, pp. 393-404.
R.J. Akhurst et al., "Genetic events and the role of TGF beta in epithelial tumour progression", J. Pathol. 1999, vol. 187, pp. 82-90 (the year of publication is sufficiently earlier than the effective U.S. filing date and any foreign priority date so that the particular month of publication is not in issue).

(Continued)

*Primary Examiner* — Julie Ha
(74) *Attorney, Agent, or Firm* — Peter B. Scull; Hamilton, DeSanctis & Cha, LLP

(57) ABSTRACT

A method to inhibit the formation of skin tumors at early stages and their subsequent progression to carcinoma in a mammal is described, the method including the topical application to the mammal's skin of a composition that includes a therapeutically effective amount of disitertide, together with pharmaceutically acceptable carriers or diluents.

9 Claims, 1 Drawing Sheet

(56) References Cited

OTHER PUBLICATIONS

Santiago, B. et al. "Topical application of a peptide inhibitor of transforming growth factor-beta 1 ameliorates bleomyci-induced skin fibrosis" J. Invest. Dermatol. Sep. 2005, vol. 125, pp. 450-455.
Serrati, S. et al. "TGF beta 1 antagonistic peptides inhibit TGF beta 1-dependent angiogenesis". Biochemical Pharmacology, Mar. 2008, vol. 77, pp. 813-825, Elsevier, Inc.
International Search Report for International Application No. PCT/EP2010/070121, mailed Mar. 6, 2009, Spain Patent Office, Madrid, 7 pages.
International Preliminary Report on Patentability International Application No. PCT/EP2010/070121, mailed Sep. 6, 2011, The Internal Bureau of Wipo, Geneva, Switzerland, 5 pages.

* cited by examiner

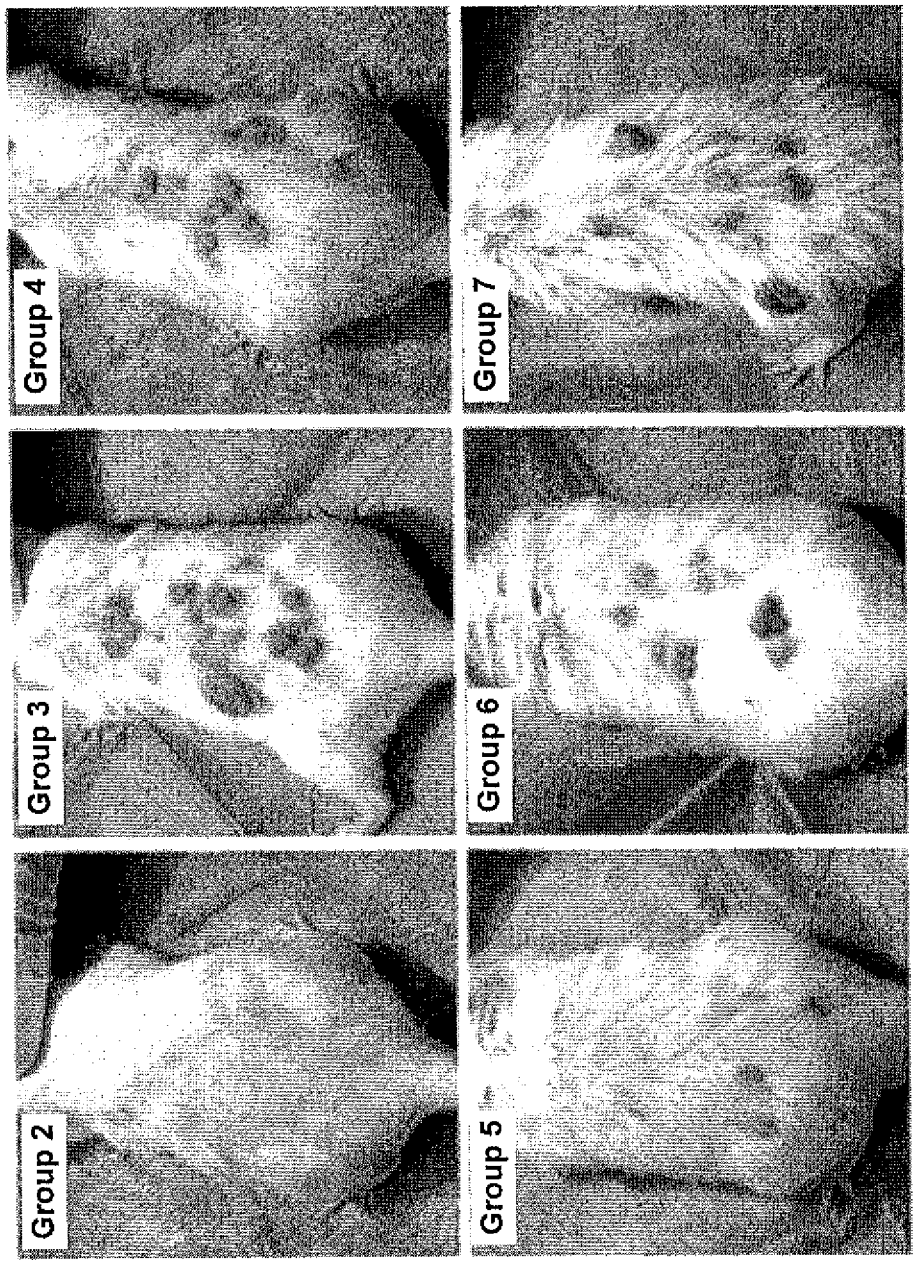

```
                              SEQUENCE LISTING

<160> NUMBER OF SEQ ID NOS: 2

<210> SEQ ID NO 1
<211> LENGTH: 14
<212> TYPE: PRT
<213> ORGANISM: Artificial sequence
<220> FEATURE:
<223> OTHER INFORMATION: disitertide peptide

<400> SEQUENCE: 1

Thr Ser Leu Asp Ala Ser Ile Ile Trp Ala Met Met Gln Asn
1               5                  10

<210> SEQ ID NO 2
<211> LENGTH: 12
<212> TYPE: PRT
<213> ORGANISM: Artificial sequence
<220> FEATURE:
<223> OTHER INFORMATION: P54 peptide

<400> SEQUENCE: 2

Thr Ser Leu Asp Ala Thr Met Ile Trp Thr Met Met
1               5                  10
```

PEPTIDE FOR THE PROPHYLACTIC OR THERAPEUTIC TREATMENT OF SKIN TUMORS IN INITIAL STAGES

CROSS-REFERENCE TO RELATED APPLICATIONS

This application is being filed under 35 USC 371 as a National Stage Application of pending International Application No. PCT/EP2010/070121 filed Mar. 4, 2010, which claimed priority to Spanish Patent Application P200900694, Filed Mar. 6, 2009, which are hereby incorporated by reference herein in their entireties for all they teach and disclose.

The invention refers to the prophylactic or therapeutic treatment of skin tumors at early stages. More specifically, the invention refers to the use of an inhibitor peptide of TGF-$\beta1$ for the prophylactic or therapeutic treatment of skin tumors at early stages, preferably by means of topical application.

STATEMENT REGARDING SEQUENCE LISTING

The Sequence Listing associated with this application is provided in text format in lieu of a paper copy, and is hereby incorporated by reference into the specification. The name of the text file containing the sequence Listing is 14455_1002US01_Sequence_Listing.txt. The text file is 1 KB, wsa created on Nov. 17, 2011, and is being submitted electronically via EFS-Web.

BACKGROUND ART

Skin cancer is a malignant growth of determined cell types on the skin that may have many causes, though solar radiation is one of the best known. Skin cancer generally develops in the epidermis, the outermost layer of the skin, but can also be located in the dermis. The most common kinds of skin cancer are basal cell carcinoma (BCC), squamous cell carcinoma (SCC) and melanoma. Basal cell carcinoma tends to grow slowly and rarely spreads. Squamous cell carcinoma is usually more aggressive than basal cell cancer and is more likely to spread to other parts of the body. The most dangerous kind of skin cancer is melanoma, especially malignant melanoma, which may be fatal if not treated early. Skin cancer is one of the cancers that is growing most rapidly and exceeds in number cases of lung, breast, colo-rectal or prostate cancer.

Transforming growth factor $\beta1$ (TGF-$\beta1$) is a multi-functional cytokine that regulates a variety of cell processes, such as cell proliferation, differentiation, apoptosis, remodeling of tissue and angiogenesis.

Various experimental models with genetically modified mice (W. Cui et al., "TGFbeta1 inhibits the formation of benign skin tumors, but enhances progression to invasive spindle carcinomas in transgenic mice", *Cell* 1996, vol. 86, pp. 531-542), complemented by in vitro studies of cultivated keratinocytes (G. Portella et al., "Transforming growth factor beta is essential for spindle cell conversion of mouse skin carcinoma in vivo: implications for tumor invasion", *Cell. Growth. Differ.* 1998, vol. 9, pp. 393-404), suggest that TGF-$\beta1$ has a dual function in skin carcinogenesis. It acts both as a suppressor of the carcinogenesis, promoting invasion and metastasis (R. J. Akhurst et al., "Genetic events and the role of TGF beta in epithelial tumour progression", *J. Pathol.* 1999, vol. 187, pp. 82-90). Therefore, it is to be expected that the inhibition of this factor in the last stages of carcinogenesis has a suppressor effect on malignant progression, whereas its inhibition at the initial stages of tumor development should have a stimulatory effect on the formation of benign tumors and their progression to malignant carcinoma.

The document WO 00/31135 describes for the first time the P144 peptide (whose INN is disitertide, SEQ ID NO: 1). It also describes how this peptide can be used to treat hepatic diseases, more concretely to treat hepatic fibrosis.

The document WO07048857 describes the use of disitertide as a modulating agent of immune response and in the treatment of cancer. The use of disitertide to treat cancer is in line with the above-mentioned studies, which suggest the stimulatory effect of the factor on malignant progression in the last stages of carcinogenesis.

However, at present there continues to be a need for therapy alternatives that can be applied topically for the prophylactic or therapeutic treatment of skin tumors at early stages, to avoid progression to carcinoma, and that are effective and well tolerated.

SUMMARY OF THE INVENTION

Surprisingly, it has been found that determined TGF-$\beta1$ inhibitor peptides inhibit the formation of skin tumors at initial stages and also inhibit their subsequent progression to carcinoma. In particular, it has been found that disitertide inhibits the formation of papillomas and delays their progression to carcinoma in mice.

Although it is known that disitertide might be useful in treating cancer in its advanced stages, the state of the art does not mention or suggest anything relating to the use of disitertide to treat skin tumors at early stages.

Thus, one aspect of the invention refers to a TGF-$\beta1$ inhibitor peptide for use in the preventive or therapeutic treatment of skin tumors at early stages, in which the peptide is disitertide or a derivative thereof.

Another aspect of the invention refers to a pharmaceutical composition that comprises a therapeutically effective amount of the peptide defined above, together with at least one pharmaceutically acceptable carrier, excipient or diluent, for use in the preventive or therapeutic treatment of skin tumors at early stages.

Finally, another aspect of the invention refers to the use of the peptide defined above for the manufacture of a medicament for the preventive or therapeutic treatment of skin tumors at early stages in a mammal, including a human.

This last aspect of the invention is related to a method to prevent or treat in a mammal, including a human, a skin tumor at early stages, in particular a papilloma or actinic keratosis, in which the method comprises the application to the mammal's skin of a composition that comprises a therapeutically effective amount of the peptide defined above, together with pharmaceutically acceptable carriers or diluents. In a preferred embodiment, the mammal presents with a skin tumor at early stage and the method comprises the application of the composition to the mammal's skin in order to treat the tumor and avoid its progression to carcinoma. In another preferred embodiment, the mammal does not present with a skin tumor and the method comprises applying the compound to the mammal's skin in order to prevent the tumor.

DETAILED DESCRIPTION OF THE INVENTION

As the examples show, the topical application of a peptide according to the invention to the skin of mice used as animal models protects against the development of both benign papillomas and SCEs induced by DMBA/TPA. Therefore, these results show that the peptides of the current invention are useful in the preventive or therapeutic treatment of skin tumors at early stages, such as papilloma or actinic keratosis. The peptides in the invention are preferentially applied to the skin of a human being, although if required they can also be applied to the skins of mammals in general.

Among the TGF-β1-inhibitor peptides in this invention the sequence SEQ ID NO: 1 (disitertide) or a derivative thereof is included. Disitertide (INN of peptide P144) was described for the first time in the document WO 00/31135. As described in this document, disitertide comprises the amino acids 730-743 of the type III receptor of TGF-β1 (accession number Q03167, SwissProt).

The term "tumor at early stage" refers to tumors confined to their place of development, which have not invaded surrounding tissue, and to tumors which have invaded other tissue, but the zone of invasion is confined to a local area. This definition is applicable to the vast majority of cancers, including skin cancer. Actinic or solar keratosis is considered the earliest stage of the development of skin cancer. More concretely, actinic keratosis is considered a pre-cancer and is the main precursor of SCC. Skin papillomas are considered another kind of tumor in an early stage: they are benign non-cancerous tumors.

The term "derivative or disitertide" includes mammal fragments, analogues and homologues of the sequence SEQ ID NO: 1, provided that they maintain their capacity to inhibit the biological activity of TGF-β1. The capacity of the peptides of the invention to inhibit the biological activity of TGF-β1 can be evaluated and, if required, quantified by means of the assay to inhibit growth of the My-1-Lu cell line. This is a cell line derived from bison pulmonary epithelium, whose proliferation is inhibited by TGF-β1, as described in WO 00/31135.

The term "fragment" means any amino acid sequence that is shorter by at least one amino acid than the sequence of origin SEQ ID NO: 1 and that comprises a length of consecutive amino acids, preferably of at least 6 residues, from the sequence of origin.

The term "analogue" includes peptides in which one or more amino acids of SEQ ID NO: 1 have been replaced by a different amino acid. The conservative replacements of amino acids are preferred. Conservative replacements are those in which an amino acid residue is replaced by another biologically similar residue. Examples of conservative replacements include the replacement of a hydrophobic residue such as isoleucine, valine, leucine or methionine by another or the replacement of a polar residue by another one, such as between arginine and lysine, between glutamic and aspartic acid or between glutamine and asparragine. Conservative replacements also include the use of a substituted amino acid instead of a non-substituted amino acid, provided that the peptide's capacity to inhibit the biological activity of TGF-β1 is maintained. Also included as analogues are peptides that have insertions or deletions of one or more amino acids in the SEQ ID NO: 1. These modifications (replacements, deletions or insertions) may be represented by a degree of homology of a particular peptide in relation to the SEQ ID NO: 1. Therefore, among the TGF-β1-inhibitor peptides of the present invention, peptides are also included that have at least 75% homology with the amino acid sequence of disitertide, preferably at least 85% homology and, even more preferably, at least 90% homology with this peptide, as long as their capacity of inhibiting the biological activity of TGF-β1 is maintained. In addition, the peptides of the invention may show chemical modifications in their amino acids. Hybrid or dimer fusion peptides that comprise the sequence SEQ ID NO: 1 or their fragments are also included as analogues.

The term "mammal homologue" includes peptides with the same biological function from species other than the human. Thus, a mammal homologue peptide of disitertide is peptide P54, with the sequence SEQ ID NO: 2, which comprises amino acids 731-742 of rat type III receptor of TGF-β1 (accession number P26342, SwissProt). According to the document WO 00/31135, disitertide is equivalent to the P54 peptide. The capacity of both disitertide and peptide P54 to act as TGF-β1 inhibitors has been shown previously, as described in the document WO 00/31135.

In a preferred embodiment, the peptide for use in the preventive or therapeutic treatment of skin tumors at early stages is disitertide (SEQ ID NO: 1).

Preferably, the peptide of the present invention is useful as an inhibitor of the generation of skin papillomas and their progression to carcinoma. Still more preferably, the peptide of the present invention is useful in the preventive or therapeutic treatment of actinic keratosis.

The peptides of the invention can be obtained by conventional methods, e.g. through techniques of solid phase chemical synthesis and purified through High-Performance Liquid Chromatography (HPLC), such as that described in WO 00/31135. If required, they can be analyzed by means of conventional techniques, such as sequencing and mass spectrometry, analysis of amino acids, nuclear magnetic resonance, etc. Alternatively, the peptides of the invention can be obtained through recombinant DNA technology.

Within the scope of this invention are found the pharmaceutically acceptable salts of the peptide of the invention. The term "pharmaceutically acceptable salts" includes the salts habitually used to form metal salts or acid addition salts. The nature of the salt is not critical, as long as it is pharmaceutically acceptable. The pharmaceutically acceptable salts of the peptide of the invention can be obtained from organic or inorganic acids or bases. These salts can be obtained by conventional methods that are well known to those skilled in the art.

The peptide can be administered by any administration pathway. Preferably, the peptide of the invention is administered topically.

Therefore, in another aspect, the invention is related to a pharmaceutical composition that comprises a therapeutically effective amount of the peptide of the invention together with at least one pharmaceutically acceptable excipient, diluent or carrier for use in the preventive or therapeutic treatment of skin tumors at early stages. The pharmaceutical composition of the present invention may contain one or more peptides of the invention, optionally, along with one or more alternative TGF-β1 inhibitor compounds. This pharmaceutical composition is useful for administering to the body of a mammal, preferably the human body. The pharmaceutical composition of the present invention is, preferably, a topical composition and may take the form of, for example, a lotion, pomade, gel, cream, patch or spray.

The amount of peptide or pharmaceutically acceptable salt of the peptide that is present in the pharmaceutical composition of the present invention may vary within a broad range. The doses for the preventive or therapeutic treatment of skin tumors in the initial stages with the peptides and/or pharmaceutical compositions of the invention will depend on numerous factors, including age, state of the patient, severity of the disease or pathological disturbance, the route and frequency of administration and also on the peptide of the invention to be administered.

The use of peptides of the invention in the production of this pharmaceutical composition is an additional aspect of this invention.

In a preferred embodiment, the invention is related to the use of a peptide of the invention for the manufacture of a medicament to inhibit the generation of papillomas and their progression to carcinoma. In another preferred embodiment, the invention is related to the use of a peptide of the invention for the manufacture of a medicament for the preventive or therapeutic treatment of actinic keratosis.

Throughout the description and the claims, the word "comprises" and its variants do not pretend to exclude other technical characteristics, additives, components or steps.

For those skilled in the art, other objects, benefits and characteristics of the invention will follow from, in part, the description and, in part, the practice of the invention.

BRIEF DESCRIPTION OF THE DRAWINGS

FIG. 1 shows images of the dorsal skin of treated mice representative of different groups, as described in the examples.

EXAMPLES

The following examples are provided by way of illustration and it is not suggested that they restrict the scope of the present invention.

Example 1

Preparation of a Topical Formulation

One vehicle topical formulation was prepared and one containing disitertide (300 µg/g). The vehicle formulation was prepared by mixing the following components: 10% dimethicone, 43.5% liquid paraffin, 0.02% methylparaben, 0.01% propylparaben, 0.5% cetrimide and 1.5% cetostearyl alcohol. This mixture was heated to 50-60° C. and emulsified with 100% purified water (also to 50-60° C.). The disitertide formulation was prepared in the same way, except that the water was replaced by a mix of water plus 0.03% disitertide previously dissolved in 0.2 ml dimethyl sulfoxide (0.22% p/p).

Example 2

Effect of Disitertide on the Formation of Papillomas and on the Development and Progression of Already Established Papillomas Material and Methods
Animals Female Swiss albino mice (aged 4-6 weeks) acquired from Harlan S.L. (Barcelona, Spain) were used. Before being treated, the animals were subjected to a 1-2 week period of adaptation under conventional temperature and moistness conditions. They were provided with sterile water and a standard diet ad libitum. All animal experiments were approved and conducted according to the institution's guidelines for the care and use of experimental animals.

Chemical Carcinogenesis

The protocol of chemical carcinogenesis in mouse skin in two stages was applied. Mouse skin is an epithelial tissue with certain benefits as an experimental model for studying the changes associated with neoplastic development. This protocol involves the treatment of mice with a single dose of a carcinogenic initiator, concretely 7,12-dimethylbenz($\alpha$)anthracene (DMBA), followed by repeated applications of the tumor promoter, 12-O-tetradecanoil phorbol-13-acetate (TPA). This treatment causes benign tumors to appear (papillomas). Most benign papillomas disappear or return, but a small fraction of them (5-10%) progress to malignant squamous cell carcinoma (SCC), which cross the basal membrane and steadily invade the underlying dermis, the subcutaneous tissue and the muscle.

The tumors were induced on the shaved dorsal skin of mice aged 6-8 weeks through a single topical application of DMBA (32 µg in 200 µl of acetone), followed by treatment twice a week with 12.5 µg of TPA in 200 µl of acetone ($10^{-4}$ M) for 12 weeks. In addition, groups of mice were treated with a topical formulation in the form of cream that contained disitertide or not, as specified below. Each week the number of tumors bigger than 2 mm in diameter were recorded in each mouse. At the end of the experiment, the animals were anesthetized and killed (32 weeks after the initiation with DMBA), and the tumors were fixed in 10% formaldehyde and embedded in paraffin for the histological studies.

Experimental Design for Treatments with Disitertide

In order to test the possible tumor-promoting effect of disitertide, TPA was replaced by a treatment with a topical formulation cream containing disitertide (group 2, consisting of 5 animals) or with vehicle only (group 1, consisting of 5 mice) during the promotion phase of chemical carcinogenesis. Similarly, the possible carcinogenic activity of disitertide was analyzed in a group of 5 mice by repeated applications of disitertide every 2 days for 23 weeks. Since papillomas appear at around 7-8 weeks post-initiation, mice initiated with DMBA and promoted with TPA were further treated with disitertide every 2 days for 4 and 12 weeks (groups 5 and 6, respectively, 10 animals each), in order to test whether disitertide could prevent skin carcinogenesis. Treatment with disitertide started in the same week in which mice were initiated with DMBA (week 0), and applications with this and TPA were performed on alternate days. As a control, a group of mice (group 4, consisting of 5 animals) were treated with vehicle only (control cream) for 12 weeks. Finally, a group of animals with tumors (group 7, consisting of 10 animals) were treated with disitertide every 2 days for 20 weeks from week 12 to week 32 after initiation with DMBA. This group of mice was included in order to test a possible anti-tumor effect of the peptide. Disitertide was applied at a dose of 60 µg in 200 µl of the topical formulation as cream, except for mice of group 7 in which the dose of disitertide was increased up to 120 µg (in 400 µl of cream).

Results

Groups of mice were subjected to chemical skin carcinogenesis by initiation with a single dose of DMBA followed by promotion twice a week with TPA for 12 weeks. This treatment gave rise to the appearance of multiple papillomas from 8 weeks after initiation with DMBA. In addition, two groups of animals were treated every 2 days with a skin cream containing disitertide for 4 and 12 weeks, starting the same day as DMBA was started (groups 5 and 6, respectively). In both cases, 30-60% fewer benign papillomas appeared than in untreated mice (group 3) or in mice treated with vehicle only (group 4), as seen at 10 and 14 weeks post-initiation (Table 1, FIG. 1). Interestingly, the shorter treatment with disitertide (4 weeks) had a more profound effect in inhibiting the number and size of papillomas.

We also tested whether disitertide could replace TPA as a promoter of carcinogenesis. To this end, mice initiated with DMBA were promoted with the cream containing disitertide or with vehicle only for 12 weeks (groups 2 and 1, respectively). As expected, no tumors were induced in these groups, except for two mice in group 1 promoted with vehicle only, which both spontaneously developed a small tumor (<5 mm in diameter) at 30 weeks post-initiation (Table 1). Disitertide showed no deleterious effect on normal skin after repeated applications every 2 days for more than 20 weeks (data not shown). These results indicate that application of disitertide to the skin in a topical cream formulation cannot initiate or promote carcinogenesis. On the contrary, topical application of disitertide had a protector effect against chemical skin carcinogenesis.

To analyze the effect of disitertide on the development and progression of already established papillomas, we included a group of mice (group 7), in which application of P144 started on week 12 after initiation with DMBA, when each mouse had about 7-8 papillomas on average (Table 1), and lasted for 20 weeks. No significant reduction in the number or size of papillomas was observed in this group. In fact, 14 weeks after initiation, the mean number of tumors >2 mm in diameter per mouse tended to level out in all groups (Table 1). The same occurred with the mean number of tumors >5 mm in diameter (Table 2). However, 32 weeks after initiation, the numbers of both tumors >2 mm and tumors >5 mm in diameter were, in general, lower in the groups treated with disitertide. Again, the most significant reduction was observed in the group treated for 4 weeks post-initiation (Tables 1 and 2).

Early papillomas are generally small (see FIG. 1), but as they become larger they adopt a cauliflower-like structure with either a narrow or a broad base. SCCs, on the other hand, are usually endophytic tumors that present as plates with an ulcerated surface. On the basis of these characteristics, we examined each mouse for the presence of carcinomas every week. As shown in Table 3, the first observable carcinoma in the control mice (groups 3 and 4) and in the mice treated with disitertide for 4 weeks (group 5) occurred at weeks 17-18 post-initiation. Notably, mice treated with disitertide during weeks 12 to 32 (group 7), which had papillomas at the beginning of the treatment, showed a delay of about 14 weeks in the first appearance of carcinomas. Mice treated with disitertide for 12 weeks post-initiation (group 6) had a shorter delay of about 6 weeks. These results show that topical application of disitertide to the skin not only prevents tumor formation but also postpones malignant conversion.

TABLE 2

Evolution of the size of the tumor in mice subjected to carcinogenesis with DMBA/TPA and treated or otherwise with disitertide

| | | Treatment | | Mean number of tumors >5 mm in diameter per mouse at the weeks indicated after initiation | | |
|---|---|---|---|---|---|---|
| Group | N° of mice | Cream | Period of time (weeks) | 14 | 25 | 32 |
| 3 | 10 | — | — | 1.6 | 4.2 | 3.9 |
| 4 | 5 | Control | 0-12 | 0.0 | 3.8 | 5.0 |
| 5 | 10 | disitertide | 0-4 | 0.1 | 3.3 | 2.3 |
| 6 | 10 | disitertide | 0-12 | 0.2 | 3.3 | 3.7 |
| 7 | 10 | disitertide | 12-32 | 0.7 | 3.1 | 3.8 |

TABLE 3

Appearance of the first carcinoma in mice subjected to carcinogenesis by DMBA/TPA and treated or otherwise with disitertide

| | | Treatment | | |
|---|---|---|---|---|
| Group | N° of mice | Cream | Period of time (weeks) | Weeks after initiation* |
| 3 | 10 | — | — | 17 |
| 4 | 5 | Control | 0-12 | 18 |
| 5 | 10 | disitertide | 0-4 | 18 |
| 6 | 10 | disitertide | 0-12 | 24 |
| 7 | 10 | disitertide | 12-32 | 32 |

*The time of appearance of the carcinomas was calculated by visual observation

The above results in mice show that disitertide can protect against chemical skin carcinogenesis. The topical application of disitertide to the skin during the promotion of tumors with TPA reduced the early appearance of benign papillomas. In addition, when the topical formulation comprising disitertide was applied directly to the surface of the tumors, their conversion from papillomas to malignant carcinomas was delayed. These results show the protective effect of disitertide against the appearance of skin cancer.

TABLE 1

Effect of disitertide on the development of a skin tumor in mouse after carcinogenesis in two stages

| | | Carcinogenesis (initiator: DMBA) | Treatment | | Mean number of tumors per mouse at the weeks indicated post-initiation | | | |
|---|---|---|---|---|---|---|---|---|
| Group | N° of mice | Promoter | Cream | Period of time (weeks) | 10 | 14 | 25 | 32 |
| 1 | 5 | Control cream | — | — | 0.0 | 0.0 | 0.0 | 0.4 |
| 2 | 5 | disitertide cream | — | — | 0.0 | 0.0 | 0.0 | 0.0 |
| 3 | 10 | TPA | — | — | 6.4 | 11.9 | 9.4 | 10.7 |
| 4 | 5 | TPA | Control | 0-12 | 8.4 | 11.8 | 12.6 | 13.5 |
| 5 | 10 | TPA | disitertide | 0-4 | 2.3 | 7.0 | 10.3 | 7.8 |
| 6 | 10 | TPA | disitertide | 0-12 | 4.7 | 8.1 | 8.1 | 8.7 |
| 7 | 10 | TPA | disitertide | 12-32 | 6.8 | 12.6 | 10.2 | 8.8 |

The invention claimed is:

1. A method to inhibit the formation of skin tumors at early stages and their subsequent progression to carcinoma in a mammal, the method comprising the topical application to the mammal's skin of a composition that comprises a therapeutically effective amount of disitertide (SEQ ID NO: 1) or its mammal homologue peptide P54 (SEQ ID NO: 2), together with pharmaceutically acceptable carriers or diluents, wherein the skin tumors at early stage are skin tumors confined to their place of development, which have not invaded surrounding tissue, or tumors which have invaded other tissue, but the zone of invasion is confined to a local area.

2. The method according to claim 1, wherein the peptide is disitertide.

3. The method according to claim 1, wherein the skin tumor at early stages is a papilloma.

4. The method according to claim 3, wherein the peptide is disitertide.

5. The method according to claim 1, wherein the skin tumor at early stages is actinic keratosis.

6. The method according to claim 5, wherein the peptide is disitertide.

7. The method according to claim 1, wherein the mammal is a human.

8. The method according to claim 3, wherein the mammal is a human.

9. The method according to claim 5, wherein the mammal is a human.

* * * * *